(12) United States Patent
Gloanec et al.

(10) Patent No.: US 8,309,341 B2
(45) Date of Patent: Nov. 13, 2012

(54) 2-MERCAPTOCYCLOPENTANECARBOXYLIC ACID COMPOUNDS, A PROCESS FOR THEIR PREPARATION AND PHARMACEUTICAL COMPOSITIONS CONTAINING THEM

(75) Inventors: Philippe Gloanec, Marly le Roi (FR); Guillaume De Nanteuil, Suresnes (FR); Jean-Gilles Parmentier, Issy les Moulineaux (FR); Anne-Françoise Guillouzic, Nanterre (FR); Tony Verbeuren, Vernouillet (FR); Alain Rupin, Savonnieres (FR); Philippe Mennecier, Conflans Sainte Honorine (FR); Marie-Odile Vallez, Montreuil (FR); Jean-Charles Quirion, Bourg-Achard (FR); Philippe Jubault, Preaux (FR); Nicolas Boyer, Saint Jeoire en Faucigny (FR)

(73) Assignees: Les Laboratories Server, Suresnes Cedex (FR); L'Institut National des Sciences Appliquées de Rouen, Saint-Étienne-du-Rouvray Cedex (FR); Le Centre National de la Recherche Scientifique, Paris Cedex (FR); L'Universite de Rouen, Mont-Saint-Aignan Cedex (FR)

( * ) Notice: Subject to any disclaimer, the term of this patent is extended or adjusted under 35 U.S.C. 154(b) by 368 days.

(21) Appl. No.: 12/803,405

(22) Filed: Jun. 25, 2010

(65) Prior Publication Data

US 2010/0330064 A1 Dec. 30, 2010

(30) Foreign Application Priority Data

Jun. 26, 2009 (FR) ..................... 09 03111

(51) Int. Cl.
*C12N 9/64* (2006.01)
*A61K 38/49* (2006.01)
*C12N 9/14* (2006.01)
*C12N 9/48* (2006.01)
*C12N 9/50* (2006.01)
*C12N 9/00* (2006.01)
*A61K 38/43* (2006.01)
*A61K 38/46* (2006.01)
*A61K 38/48* (2006.01)

(52) U.S. Cl. ........ 435/226; 435/183; 435/195; 435/212; 435/215; 435/219; 424/94.1; 424/94.6; 424/94.63; 424/94.67; 514/114; 514/317; 514/548; 546/238; 560/192; 562/504

(58) Field of Classification Search .................. None
See application file for complete search history.

(56) References Cited

FOREIGN PATENT DOCUMENTS
WO WO 03/080631 10/2003

OTHER PUBLICATIONS

Adler, M. et al "Crystal Structures of Potent Thiol-Based Inhibitors Bound to Carboxypeptidase B" Biochem. 2005, 44(26), pp. 9339-9347.*
Adler, M. et al "Crystal Structures of Potent Selective Peptide Mimetics Bound to Carboxypeptidase B" Acta Cryst., Feb. 2008 (published online Jan. 16, 2008), D64(2), pp. 149-157.*
Wang, Y-X, et al "A Novel Inhibitor of Activated Thrombin Activatable Fibrinolysis Inhibitor (TAFIa)—Part II: Enhancement of Both Exogenous and Endogenous Fibrinolysis in Animal Models of Thrombosis" Thromb Haemost 2007 (published online Dec. 8, 2006), 97, pp. 54-61.*
Polla, M.O. et al "Design and Synthesis of Potent, Orally Active, Inhibitors of Carboxypeptidase U (TAFIa)." Bioorg Med Chem. Mar. 1, 2004, 12(5), pp. 1151-1175.*
Do Y H, et al., "Inhibition of thrombin activatable fibrinolysis inhibitor by cysteine derivatives" Thrombosis Research, vol. 116, No. 3, p. 265-271, Jan. 1, 2005.
French Preliminary Search Report for FR09/03111 of Feb. 4, 2010, 2 pages.

* cited by examiner

*Primary Examiner* — Chris R Tate
*Assistant Examiner* — Aaron J Kosar
(74) *Attorney, Agent, or Firm* — Hueschen and Sage

(57) ABSTRACT

Compounds of formula (I):

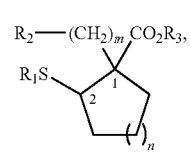

(I)

wherein:
$R_1$ represents a hydrogen atom or a group of formula $COR_4$, or $R_1$ represents a group of formula (A):

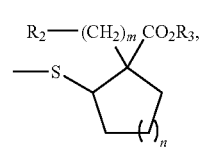

(A)

$R_2$ represents a group of formula $NR_5R_6$, or $R_2$ represents a nitrogen-containing heterocyclic group, an aryl group or a heteroaryl group,
$R_3$ represents a hydrogen atom or an alkyl group,
m represents an integer between 1 and 6 inclusive,
n represents 0, 1 or 2,
their optical isomers, and also addition salts thereof with a pharmaceutically acceptable acid.
Medicinal products containing the same which are useful in treating and/or preventing thrombotic events.

13 Claims, No Drawings

2-MERCAPTOCYCLOPENTANECARBOXYLIC ACID COMPOUNDS, A PROCESS FOR THEIR PREPARATION AND PHARMACEUTICAL COMPOSITIONS CONTAINING THEM

The present invention relates to new 2-mercaptocyclopentanecarboxylic acid compounds, to a process for their preparation and to pharmaceutical compositions containing them.

The compounds of the invention are inhibitors of TAFIa (activated thrombin-activatable fibrinolysis inhibitor).

TAFI (also referred to as plasma procarboxypeptidase B, procarboxypeptidase R or procarboxypeptidase U) is a plasma glycoprotein of 60 kDa, produced by the liver, which circulates in the form of a zymogen. During blood coagulation and fibrinolysis, thrombin and plasmin cleave the pro-segment of TAFI at the Arg92-Ala93 bond to convert it into an active enzyme, TAFIa, which has a half-life of from 8 to 15 minutes at 37° C. Cleavage of the prosegment by thrombin is accelerated by thrombomodulin, a cofactor present in plasma and on the surface of vascular endothelial cells (Bouma B N and Meijers J C, *Thrombin-activatable fibrinolysis inhibitor*, 2003, Journal of Thrombosis and Haemostasis, 1: 1566-1574). TAFIa negatively regulates fibrinolysis by cleaving the C-terminal lysine residues of the fibrin fibres which appear on partial degradation of the fibrin by the first traces of plasmin. These C-terminal lysine residues on the partially degraded fibrin act as ligands of circulating plasma plasminogen and of the tissue plasminogen activator (tPA) generated by endothelial cells in the case of thrombotic ischaemia. They accordingly make it possible to localise the conversion of plasminogen into plasmin by tPA without interference either with the circulating plasmin inhibitor α2-antiplasmin or with the circulating inhibitor of tissue plasminogen activator (PAI-1). Cleavage of the C-terminal lysine sites by TAFIa therefore reduces the rate at which plasmin is generated. Endogenous fibrinolysis is then inhibited and reduces the lysis of fibrinous arterial and venous thromboses and also the therapeutic thrombolysis undertaken in patients in the post-thrombotic acute ischaemic phase. Inhibitors of TAFIa therefore have the potential to increase the endogenous and therapeutic fibrinolysis potential and to act as anti-thrombotic and pro-fibrinolytic agents without major haemorrhagic risk because they interfere neither with platelet activation nor with coagulation during haemostasis of the blood.

The property of inhibiting TAFIa accordingly makes it possible to consider using the compounds of the invention in the treatment and prevention of thrombotic events in at-risk patients.

Their use will be valuable in the treatment, prevention and secondary prevention of vascular complications, more especially cardiovascular, pulmonary and cerebrovascular complications, associated with atherothrombotic diseases, atherosclerosis, diabetes, hyperlipidaemia, hypertension, chronic venous diseases, metabolic syndrome associated with obesity, and cancer. The compounds according to the invention are especially useful in the treatment, prevention and secondary prevention of myocardial infarction, angina pectoris, cerebrovascular accidents, aortic aneurysms, arteritis of the lower limbs, venous thromboses and pulmonary embolism.

Vascular risk factors and vascular diseases such as hypertension, obesity, diabetes, heart disease, cerebrovascular diseases and hyperlipidaemia and therefore atherosclerosis play a part in the genesis of dementias such as Alzheimer's disease and vascular dementia (Qiu C., De Ronchi D. and Fratiglioni L., *The epidemiology of the dementias: an update*, 2007, Current Opinion in Psychiatry, 20: 380-385). The compounds of the invention will accordingly also be useful in the treatment and/or prevention of dementias such as Alzheimer's disease and vascular dementia.

TAFIa reduces the endogenous fibrinolytic potential. As inhibitors of TAFIa, the compounds of the present invention are therefore useful as adjuncts to acute treatment with injectable fibrinolytic agents such as recombinant tPA (for example, alteplase, tenecteplase, reteplase), recombinant uPA or streptokinase, which are used in emergency situations (for example, myocardial infarction, cerebrovascular accident).

The compounds of the present invention reinforce the activity of those injectable fibrinolytic agents and therefore result in their being used with fewer haemorrhagic and neurotoxic risks (their dose being lowered and, therefore, their side effects reduced).

The present invention relates more specifically to compounds of formula (I):

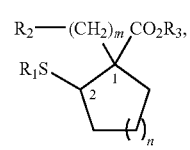

wherein:
$R_1$ represents a hydrogen atom or a group of formula $COR_4$ wherein $R_4$ represents a linear or branched $C_1$-$C_6$alkyl group or an aryl group,
or $R_1$ represents a group of formula (A):

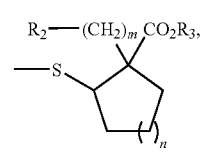

$R_2$ represents a group of formula $NR_5R_6$ wherein $R_5$ and $R_6$, which are the same or different, each represent a hydrogen atom or a linear or branched $C_1$-$C_6$alkyl group, or $R_2$ represents a nitrogen-containing heterocyclic group, an aryl group or a heteroaryl group,
$R_3$ represents a hydrogen atom or a linear or branched $C_1$-$C_6$alkyl group,
m represents an integer between 1 and 6 inclusive,
n represents 0, 1 or 2,
to their optical isomers, and also to addition salts thereof with a pharmaceutically acceptable acid.

An aryl group is understood to be phenyl optionally substituted by one or more identical or different groups selected from halogen, linear or branched ($C_1$-$C_6$)alkyl, linear or branched ($C_1$-$C_6$)alkoxy, amino (optionally substituted by one or two linear or branched ($C_1$-$C_6$)alkyl groups) and aminoalkyl, the amino group optionally being substituted by one or two linear or branched ($C_1$-$C_6$)alkyl groups.

A heteroaryl group is understood to be a 5- to 12-membered, mono- or bi-cyclic, aromatic group containing one, two or three hetero atoms selected from oxygen, nitrogen and sulphur, it being understood that heteroaryl may optionally be substituted by one or more identical or different groups selected from halogen, linear or branched ($C_1$-$C_6$)alkyl, linear or branched ($C_1$-$C_6$)alkoxy, amino (optionally substituted by one or two linear or branched ($C_1$-$C_6$)alkyl groups) and aminoalkyl, the amino group optionally being substituted by one or two linear or branched ($C_1$-$C_6$)alkyl groups.

Among heteroaryl groups there may be mentioned, without implying any limitation, the groups thienyl, pyridyl, furyl, pyrrolyl, imidazolyl, oxazolyl, isoxazolyl, thiazolyl, isothiazolyl, pyrimidinyl, pyrazinyl, pyridazinyl.

A nitrogen-containing heterocyclic group is understood to be a 4- to 7-membered, saturated or unsaturated, monocyclic group containing one or more nitrogen atoms and optionally one or more other hetero atoms selected from oxygen and sulphur.

Among nitrogen-containing heterocyclic groups there may be mentioned, without implying any limitation, the groups azetidinyl, pyrrolidinyl, piperidyl and piperazinyl.

Optical isomers are understood to be diastereoisomers and enantiomers.

The compounds of formula (I) contain at least two asymmetric centres (in positions 1 and 2 of the ring) and may therefore exist in the form of a single enantiomer, a single diastereoisomer or in the form of a mixture of diastereoisomers.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid, camphoric acid.

One aspect of the present invention relates to compounds of formula (I) wherein $R_1$ represents a hydrogen atom.

Another aspect of the present invention relates to compounds of formula (I) wherein $R_2$ represents an amino group.

Another aspect of the present invention relates to compounds of formula (I) wherein $R_2$ represents a pyridyl group.

Another aspect of the present invention relates to compounds of formula (I) wherein $R_3$ represents a hydrogen atom.

Another aspect of the present invention relates to compounds of formula (I) wherein m represents 3.

Another aspect of the present invention relates to compounds of formula (I) wherein n represents 1.

Another aspect of the present invention relates to compounds of formula (Ia), a particular case of the compounds of formula (I):

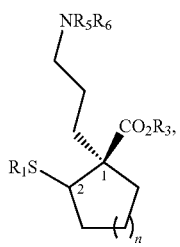

(Ia)

wherein n, $R_1$, $R_3$, $R_5$ and $R_6$ are as defined in formula (I).

Another aspect of the invention relates to the following compounds of formula (I):
  (1R,2S)-1-(3-aminopropyl)-2-mercaptocyclopentanecarboxylic acid, and also its optical isomers and addition salts thereof with a pharmaceutically acceptable acid,
  (1R,2S)-2-acetylthio-1-(3-aminopropyl)-cyclopentanecarboxylic acid, and also its optical isomers and addition salts thereof with a pharmaceutically acceptable acid.

The present invention relates also to a process for the preparation of compounds of formula (I), starting from the compound of formula (II):

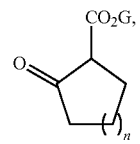

(II)

wherein n represents 0, 1 or 2, and G represents a protecting group for the carboxy function, which is reacted with a compound of formula (III):

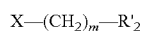

(III), wherein X represents a halogen atom or a triflate, tosylate or mesylate group,
m represents an integer between 1 and 6 inclusive,
and $R'_2$ represents a group of formula $NR'_5R'_6$ wherein $R'_5$ and $R'_6$, which may be the same or different, each represent a protecting group for the amino function or a linear or branched $C_1$-$C_6$alkyl group, or $R'_2$ represents a nitrogen-containing heterocyclic group optionally substituted by a protecting group for the amino function, or $R'_2$ represents an aryl or heteroaryl group,
to yield the compound of formula (IV):

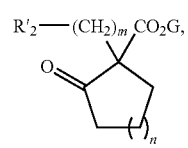

(IV)

wherein $R'_2$, G, m and n are as defined hereinbefore,
which is subjected to a reducing agent for the oxo function,
to yield a compound of formula (V):

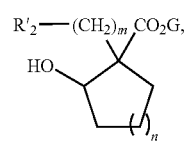

(V)

wherein $R'_2$, G, m and n are as defined hereinbefore,
which is reacted with mesyl chloride, tosyl chloride, triflic anhydride or a halogenating reagent to yield the compound of formula (VI):

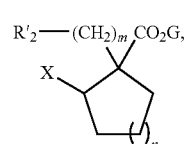

(VI)

wherein $R'_2$, G, m and n are as defined hereinbefore, and X represents a mesylate, tosylate or triflate group or a halogen atom, the diastereoisomers of which are separated when it is desired to obtain a compound of formula (I) in the form of a single diastereoisomer, and which is then reacted with a compound of formula (VII):

wherein M represents potassium, sodium or lithium, and R'₁ represents an alkyl or aryl group, to yield the compound of formula (VIII):

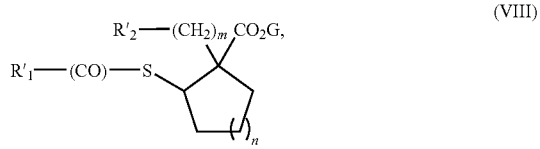

wherein R'₁, R'₂, G, m and n are as defined hereinbefore, the enantiomers of which are separated by chiral chromatography when it is desired to obtain a compound of formula (I) in the form of a single enantiomer, the thiol, amino and carboxy functions of which are, where applicable, deprotected to yield the compound of formula (I), which, when it is desired to obtain an addition salt of the compound of formula (I) with a pharmaceutically acceptable acid, is reacted with the corresponding acid.

The present invention relates also to a process for the preparation of compounds of formula (Ia), a particular case of the compounds of formula (I) wherein m represents 3 and R₂ represents NR₅R₆, starting from the compound of formula (II):

wherein n represents 0, 1 or 2, and G represents a protecting group for the carboxy function, which is reacted with acrolein, in the presence of an asymmetric catalyst such as for example, catalyst Q or QD, depending on whether it is desired to obtain the compound of configuration (1R) or (1S),

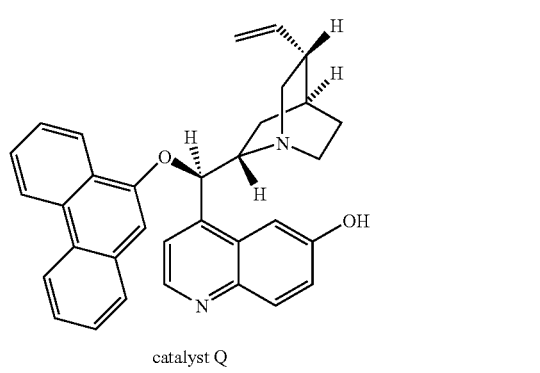

catalyst Q

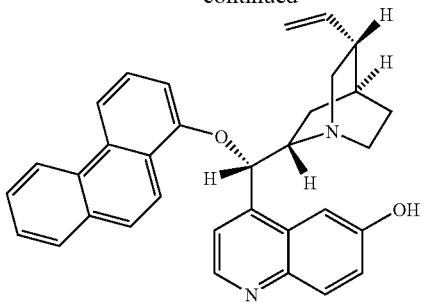

catalyst QD to yield the compound of formula (IX), of configuration (1R) or (1S):

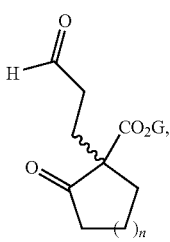

wherein n and G are as defined hereinbefore, the aldehyde function of which is reduced to yield the compound of formula (X):

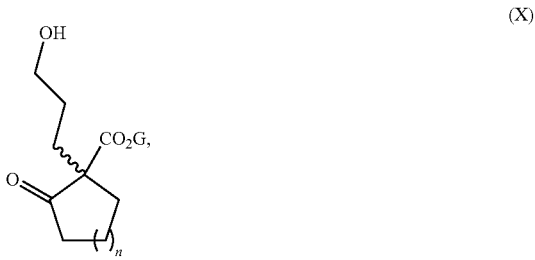

wherein n and G are as defined hereinbefore, which is reacted with mesyl chloride, tosyl chloride, triflic anhydride or a halogenating reagent to yield the compound of formula (XI):

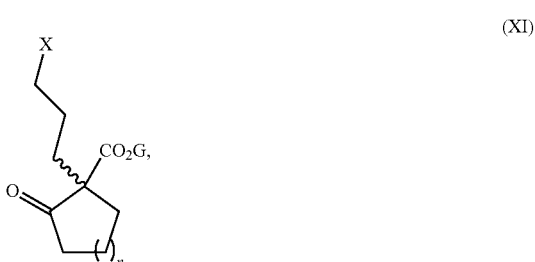

wherein n and G are as defined hereinbefore, and X represents a halogen atom or a triflate, tosylate or mesylate group, the ketone function of which is reduced with the aid of a reducing agent to yield the compound of formula (XII):

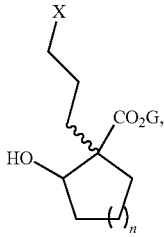

(XII)

wherein n, G and X are as defined hereinbefore, which is reacted with a compound of formula (XIII):

 (XIII), wherein $R''_5$ and $R''_6$ each represent a protecting group for the amino function or a linear or branched $C_1$-$C_6$alkyl group, to yield the compound of formula (XIV):

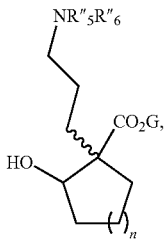

(XIV)

wherein n, G, $R''_5$ and $R''_6$ are as defined hereinbefore, which is reacted with mesyl chloride, tosyl chloride, triflic anhydride or a halogenating reagent to yield the compound of formula (XV):

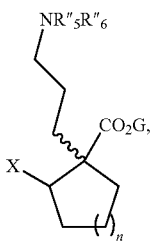

(XV)

wherein n, G, $R''_5$ and $R''_6$ are as defined hereinbefore, and X represents a mesylate, tosylate or triflate group or a halogen atom, and which is then reacted with a compound of formula (VII):

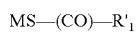 (VII), wherein M represents potassium, sodium or lithium, and $R'_1$ represents an alkyl or aryl group, to yield the compound of formula (XVI):

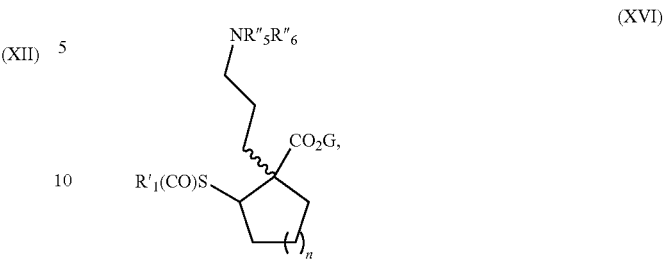

(XVI)

wherein n, $R'_1$, G, $R''_5$ and $R''_6$ are as defined hereinbefore, the thiol, amino and carboxy functions of which are, where applicable, deprotected to yield the compounds of formula (Ia):

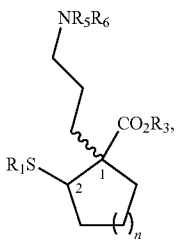

(Ia)

wherein n, $R_1$, $R_3$ $R_5$ and $R_6$ are as defined hereinbefore, which, when it is desired to obtain an addition salt of the compound of formula (Ia) with a pharmaceutically acceptable acid, are reacted with the corresponding acid.

Optically pure compounds of formula (Ia) either are obtained by asymmetric reduction of the ketone of formula (XI) using a chiral reducing agent or they are separated from the mixture of diastereoisomers at a later stage.

The compounds of the invention are inhibitors of TAFIa.

As such they are useful in the prevention or treatment of thrombotic events in at-risk patients. Their use will be valuable in the treatment and prevention of vascular complications, more especially cardiovascular, pulmonary and cerebrovascular complications, associated with atherothrombotic diseases, atherosclerosis, diabetes, hyperlipidaemia, hypertension, chronic venous diseases, metabolic syndrome associated with obesity, or cancer.

The compounds according to the invention are especially useful in the treatment, prevention and secondary prevention of myocardial infarction, angina pectoris, cerebrovascular accidents of any origin (especially atherothrombotic, cardioembolic or caused by atrial fibrillation), aortic aneurysms or arteritis of the lower limbs, venous thromboses (especially in the catheterised cancer patient) and pulmonary embolism.

Vascular risk factors and vascular diseases such as hypertension, obesity, diabetes, heart disease, cerebrovascular diseases and hyperlipidaemia and therefore atherosclerosis play a part in the genesis of dementias such as Alzheimer's disease and vascular dementia (Qiu C., De Ronchi D. and Fratiglioni L., *The epidemiology of the dementias: an update,* 2007, Current Opinion in Psychiatry, 20: 380-385). The compounds of the invention will accordingly also be useful in the treatment and/or prevention of dementias such as Alzheimer's disease and vascular dementia.

TAFIa reduces the endogenous fibrinolytic potential. As inhibitors of TAFIa, the compounds of the present invention are therefore useful as adjuncts to acute treatment with injectable fibrinolytic agents such as recombinant tPA (for example, alteplase, tenecteplase, reteplase), recombinant uPA or streptokinase, which are used in emergency situations (for example, myocardial infarction, cerebrovascular accident).

The compounds of the present invention reinforce the activity of those injectable fibrinolytic agents and therefore result in their being used with fewer haemorrhagic and neurotoxic risks (their dose being lowered and, therefore, their side effects reduced).

The present invention relates also to pharmaceutical compositions comprising a compound of formula (I), in combination with one or more inert, non-toxic, pharmaceutically acceptable excipients or carriers.

Among the pharmaceutical compositions according to the invention there may be mentioned more especially those that are suitable for oral, parenteral (intravenous, intramuscular or subcutaneous), per- or trans-cutaneous, nasal, rectal, perlingual, ocular or respiratory administration, and especially tablets or dragées, sublingual tablets, capsules, hard gelatin capsules, suppositories, creams, ointments, dermal gels, injectable or drinkable preparations, aerosols, eye drops and nose drops.

In addition to the compound of formula (I), the pharmaceutical compositions according to the invention comprise one or more excipients or carriers such as diluents, lubricants, binders, disintegrating agents, absorbents, colourants, sweeteners.

By way of example of excipients or carriers, there may be mentioned:
as diluents: lactose, dextrose, sucrose, mannitol, sorbitol, cellulose, glycerol,
as lubricants: silica, talc, stearic acid and its magnesium and calcium salts, polyethylene glycol,
as binders: aluminium silicate, magnesium silicate, starch, gelatin, tragacanth, methylcellulose, sodium carboxymethylcellulose and polyvinylpyrrolidone,
as disintegrating agents: agar, alginic acid and its sodium salt, effervescent mixtures.

The percentage of active ingredient of formula (I) in the pharmaceutical composition is preferably from 5% to 50% by weight.

The useful dosage varies according to the age and weight of the patient, the administration route, the nature and severity of the disorder, and the administration of any associated treatments and ranges from 0.5 mg to 1000 mg per day in one or more administrations.

According to one aspect of the present invention, the pharmaceutical compositions according to the present invention do not contain any active ingredient other than the compound of formula (I).

According to another aspect of the present invention, the pharmaceutical compositions according to the present invention also comprise, besides the compound of formula (I), a fibrinolytic agent, more especially an injectable fibrinolytic agent such as recombinant tPA (for example, alteplase), recombinant uPA or streptokinase. In this case, the compositions are in injectable form.

It will be possible for the tPA dose to vary in scale between 0 and 100 mg.

According to another aspect of the present invention, the pharmaceutical compositions according to the present invention comprise, besides the compound of formula (I), an anticoagulant such as, for example, warfarin, dabigatran etexilate, rivaroxaban.

It will be possible for the warfarin dose to vary in scale between 1 and 100 mg.

According to another aspect of the present invention, the pharmaceutical compositions according to the present invention comprise, besides the compound of formula (I), an antiplatelet agent such as, for example, aspirin, clopidogrel, prasugrel . . . .

It will be possible for the aspirin dose to vary in scale between 10 and 1000 mg.

It will be possible for the clopidogrel dose to vary in scale between 10 and 1000 mg.

The Examples that follow illustrate the present invention. The structures of the compounds described in the Examples were determined according to customary spectrophotometric techniques (infrared, nuclear magnetic resonance, mass spectrometry).

ABBREVIATIONS (+)-DIPCl: (+)-diisopinocampheylchloroborane ((+)-diisopinocamphenyl boron chloride)
DMAP: dimethylaminopyridine
DMF: dimethylformamide
DMSO: dimethyl sulphoxide
eq.: molar equivalent
HMPA: hexamethylphosphoramide
HPLC: High-Performance Liquid Chromatography
NMR: Nuclear Magnetic Resonance
TAFIa: activated thrombin-activatable fibrinolysis inhibitor
THF: tetrahydrofuran
tPA: tissue plasminogen activator
uPa: urokinase or urokinase-type plasminogen activator

EXAMPLE 1

(1R,2S)-1-(3-Aminopropyl)-2-mercaptocyclopentanecarboxylic acid trifluoroacetate Step A: Benzyl 2-oxo-cyclopentanecarboxylate In a 4-liter flask fitted with a Dean-Stark apparatus and a condenser, methyl 2-oxo-cyclopentanecarboxylate (380 mL; 3 mol), benzyl alcohol (342 mL; 3.3 mol; 1.1 eq.) and DMAP (18.3 g; 0.15 mol; 0.05 eq.) are dissolved in 1800 mL of cyclohexane. The reaction mixture is stirred for 48 hours at reflux (temperature of the mixture: 90° C.) and the methanol formed is distilled off. After cooling, the reaction mixture is concentrated and taken up in 1500 mL of dichloromethane. The organic phase is washed with 1N hydrochloric acid, with water, and then with saturated sodium chloride solution. It is then dried, filtered and then evaporated.

The oil thereby obtained is purified by fractional distillation under reduced pressure (128-130° C./4×10$^{-2}$ mbar) to yield the expected product.

Step B: Benzyl 1-(4-tert-butoxy-4-oxobutyl)-2-oxo-cyclopentanecarboxylate

At ambient temperature, a solution of benzyl 2-oxo-cyclopentanecarboxylate obtained in the Step above (1 g; 5.43 mmol) in 5 mL of anhydrous acetone is poured, with vigorous stirring, into a suspension of dry potassium carbonate (3 g; 21.7 mmol; 4 eq.) in 10 mL of anhydrous acetone. Vigorous stirring of the reaction mixture is continued for one hour and then tert-butyl 4-bromobutanoate (2.04 g; 9.16 mmol; 2 eq.) dissolved in 2 mL of acetone is rapidly poured in. The reaction mixture is heated at reflux overnight. After cooling, the reaction mixture is filtered and then taken up in 20 mL of dichloromethane. The organic phase is washed, dried, filtered and then evaporated.

The crude product is purified by flash chromatography on silica gel using a mixture of heptane/ethyl acetate (95/5) as eluant.

Step C: 4-{1-[(Benzyloxy)carbonyl]-2-oxocyclopentyl}butanoic acid 140 mL of trifluoroacetic acid are poured, at ambient temperature, over 20 minutes, into a solution of the tert-butyl ester obtained in the Step above (200 g; 0.545 mol) in 700 mL of anhydrous dichloromethane. The reaction mixture is stirred overnight at ambient temperature. Note: Add 10% more trifluoroacetic acid if, after stirring overnight, any starting material remains, and continue stirring for 3 hours.

The reaction mixture is evaporated and taken up in toluene (3×500 ml) in order to remove the maximum amount of trifluoroacetic acid. After drying under a pump vacuum, the crude oil obtained is taken up in sodium hydrogen carbonate solution (84 g/1 L; 2 eq.). The basic aqueous phase is then washed with ether (3×300 mL) and then re-acidified with 4N hydrochloric acid solution. The acidic aqueous phase is extracted with ethyl acetate (3×300 mL). The combined organic phases are washed, dried and evaporated. The product is used without purification in the next Step.

Step D: Benzyl 1-(3-{[benzyloxy)carbonyl]amino}propyl)-2-oxo-cyclopentanecarboxylate To a solution of the acid from the Step above (123.7 g; 0.406 mol) in 1 L of anhydrous toluene there are added, dropwise over 5 minutes, at ambient temperature, triethylamine (84.5 mL; 0.610 mol; 1.5 eq.), benzyl alcohol (75.6 mL; 0.731 mol; 1.8 eq.), and then diphenyl phosphoryl azide (96.3 mL; 0.447 mol; 1.1 eq.). The reaction mixture is stirred at reflux overnight.

After cooling, the reaction mixture is evaporated and taken up in 1 L of ethyl acetate. The ethyl acetate phase is washed with 1N hydrochloric acid solution (3×200 mL), water, saturated sodium hydrogen carbonate solution and then saturated sodium chloride solution. The organic phase is dried, filtered and then evaporated.

The crude product is purified by distilling off the impurities (mainly benzyl alcohol) from 50 to 70° C. under $4 \times 10^{-2}$ mbar.

Step E: Benzyl 1-(3-{[(benzyloxy)carbonyl]amino}propyl)-2-hydroxy-cyclopentanecarboxylate To a solution of the keto ester from the Step above (98 g; 0.239 mol) in 600 mL of anhydrous methanol there is added, at −10° C., sodium borohydride (11.4 g; 0.301 mol; 1.25 eq.) in ten portions. The reaction mixture is held at −10° C. for one hour and is then allowed to come back up to, and is stirred at, ambient temperature for two hours. After evaporating off the methanol, the reaction mixture is taken up in 1 L of ethyl acetate. The organic phase is washed with 10% ammonium chloride solution, water and then saturated sodium chloride solution. The organic phase is dried, filtered and then evaporated.

Step F: Benzyl 1-(3-{[(benzyloxy)carbonyl]amino}propyl)-2-[(methylsulphonyl)oxy]-cyclopentanecarboxylate (racemic trans diastereoisomer)

At ambient temperature, triethylamine (49.53 mL; 0.357 mol; 1.5 eq.) is added to a solution of the alcohol obtained in the Step above (98 g; 0.238 mol) in 950 mL of anhydrous tetrahydrofuran. The reaction mixture is cooled to −30° C. and then mesyl chloride (27.61 mL; 0.357 mol; 1.5 eq.) dissolved in 120 mL of anhydrous tetrahydrofuran is poured in dropwise. The mixture is allowed to come back up to, and is stirred at, ambient temperature for two hours. After evaporating off the tetrahydrofuran, the reaction mixture is taken up in 1 L of ethyl acetate. The organic phase is washed, dried, filtered and then evaporated.

The crude product is purified by flash chromatography on silica gel (5 kg) using a gradient of heptane/ethyl acetate (7/3 to 6/4) as eluant.

The trans diastereoisomer is the first in the order of elution.

Step G: Benzyl 2-(acetylthio)-1-(3-{[(benzyloxy)carbonyl]amino}propyl)cyclopentane-carboxylate (racemic cis diastereoisomer)

Preparation of Potassium Thioacetate: Very Hygroscopic—Do Not Dry—Prepare and Use Extemporaneously.

A suspension of 40 g of potassium thioacetate in 350 mL of anhydrous acetonitrile is heated at reflux for 30 minutes and is filtered, and the operation is then repeated a second time.

To a solution of the (racemic trans) mesylate from the Step above (25 g; 0.051 mol) in 800 ml of anhydrous acetonitrile there are added previously washed potassium thioacetate (45 g not filtered under suction—theory: 29.2 g; 0.255 mol; 5 eq.) and 18C6 crown ether (13.5 g; 0.051 mol; 1 eq.), and then the reaction mixture is heated at reflux for 20 hours. After cooling, the reaction mixture is filtered and the solvent is then evaporated off.

The crude product is purified by flash chromatography on silica gel (2 kg) using a gradient of heptane/ethyl acetate (8/2 to 5/5) as eluant.

Note: this first column allows pre-purification and recovery of unreacted starting material.

The portion containing the expected product (6.5 g) is purified by flash chromatography on silica gel (200 g) using a gradient of dichloromethane/ethyl acetate (99/1 to 95/5) as eluant.

Step H: Benzyl(1R,2S)-2-(acetylthio)-1-(3-{[(benzyloxy)carbonyl]amino}propyl)-cyclopentanecarboxylate The enantiomers of the racemic cis compound obtained in the Step above are separated by preparative chiral chromatography on a column of CHIRALPAK AD-H 5 μm using a mixture of $CO_2$/EtOH (80/20) as mobile phase.

The detection wavelength is 230 nm.

The (1R,2S) enantiomer=enantiomer 2 is the second in the order of elution.

Step I: Benzyl(1R,2S)-1-(3-{[(benzyloxy)carbonyl]amino}propyl)-2-mercaptocyclopentane-carboxylate To a solution of the compound obtained in the Step above (8.16 g; 0.0174 mol) in 150 mL of anhydrous and degassed dioxane there is added dropwise, at 10° C., a 1N sodium hydroxide solution (35 mL; 0.0348 mol; 2 eq.). The mixture is heated at 60° C. for 30 minutes. After cooling, the reaction mixture is neutralised by adding 35 mL 1N hydrochloric acid and is then lyophilised.

Step J: (1R,2S)-1-(3-Aminopropyl)-2-mercaptocyclopentanecarboxylic acid trifluoroacetate 600 mL of ammonia are condensed in a 2-liter reactor and, at −78° C., sodium (10 g; 0.435 mol; 25 eq.) is added in ten portions. The reaction mixture is held at −78° C. for 45 minutes. There is then added dropwise, over 30 minutes, a solution of the compound obtained in the Step above in a previously degassed mixture of tetrahydrofuran/methanol (140 mL/12 mL). Stirring is maintained at −78° C. for 1 hour, and the mixture is allowed to come back up to, and is stirred at, ambient temperature. After removing the ammonia, a solution of ammonium chloride (23.3 g in 110 mL of water) is added to the reaction mixture over 30 minutes, the tetrahydrofuran is evaporated off and then acidification with 6M hydrochloric acid solution (15 mL) is carried out. Filtration and then lyophilisation are carried out.

The crude product is desalted by preparative HPLC on a column of Kromasil using a gradient of water/acetonitrile/trifluoroacetic acid as mobile phase (100/0/0.1 for 10 minutes, then 100/0/0.1 to 70/30/0.1 over 20 minutes, followed by isocratic operation at 70/30/0.1).

The fractions containing the expected product and also the corresponding dimer (disulphide bridge) are lyophilised.

To a solution of the above lyophilisate (4.3 g) in 100 mL of acetic acid there are added 4.5 g of zinc (10 eq.) and then, with vigorous stirring, the reaction mixture is heated at 60° C. until the dimer has disappeared (about 6 hours). After cooling, the reaction mixture is filtered, the filtrate is diluted with 400 mL of water and is then lyophilised.

The crude product is purified by preparative HPLC on a column of Kromasil (1 kg–600 mm×60 mm–70 ml/min) using a mixture of water/acetonitrile/trifluoroacetic acid (85/15/0.1) as mobile phase.

The fractions containing the expected product are lyophilised.

Optical rotation: solvent: methanol, C=1, T=21° C., L=589 nm, $[\alpha]_D$=+32.46°.

CAD/MS/MS spectrum of $[M+H]^+$=204.1 in accordance with the expected structure.

EXAMPLE 2

(1R,2S)-2-Acetylthio-1-(3-aminopropyl)-cyclopentanecarboxylic acid hydrochloride To a solution of the compound of Step H of Example 1 (2.40 g; 4.72 mmoles) in 20 mL of anhydrous dichloromethane there is added dropwise, at ambient temperature, 4M HCl/dioxane solution (35.5 mL; 141.6 mmoles; 30 eq.). The reaction mixture is left at ambient temperature, with stirring, until the two functions have been deprotected (checked by LC/MS—approximate duration: overnight) and the solvents are then evaporated off. The product obtained is purified on a column of BIOGEL P2 using a mixture of water/acetonitrile/1N hydrochloric acid (1000/1000/2) as mobile phase. The fractions containing the expected product are lyophilised.

| Elemental microanalysis | C | H | N | S | Cl− |
|---|---|---|---|---|---|
| Calculated % | 46.88 | 7.15 | 4.97 | 11.38 | 12.58 |
| Found % | 46.82 | 7.2 | 5.23 | 10.828 | 13.13 |

EXAMPLE 3

(1R,2S)-1-(3-Aminopropyl)-2-mercaptocyclopentanecarboxylic acid hydrochloride

A solution of the compound of Example 2 (4.51 g; 16 mmoles) in 148 mL of 4M HCl solution is heated overnight at 45° C. After cooling, the reaction mixture is diluted with 150 mL of water and is then lyophilised.

The crude product is purified by preparative HPLC on a column of Kromasil (1 kg–600 mm×60 mm–70 ml/min) using a mixture of water/acetonitrile (95/5) as mobile phase.

The fractions containing the expected product are lyophilised.

| Elemental microanalysis | C | H | N | S | Cl− |
|---|---|---|---|---|---|
| Calculated % | 45.09 | 7.57 | 5.84 | 13.37 | 14.79 |
| Found % | 44.57 | 7.68 | 5.74 | 12.88 | 16.69 |

CAD/MS/MS spectrum of $[M+H]^+$=204.1 in accordance with the expected structure.

EXAMPLE 3a (1R,2S)-1-(3-Aminopropyl)-2-mercaptocyclopentanecarboxylic acid

Step A: Di-tert-Butyl adipate

Adipoyl chloride (629.8 g; 3.44 moles) is poured dropwise, at ambient temperature, into a solution of tert-butanol (3.27 L; 34.4 moles—10 eq.) and pyridine (800 mL; 10.32 moles—3 eq.) in 3 L of anhydrous toluene. The reaction mixture is heated at 70° C., with stirring, overnight. After cooling, the precipitate of pyridinium chloride is filtered off and rinsed with toluene. The toluene phase is washed with 1N hydrochloric acid solution (4×500 mL), 10% sodium carbonate solution (1×500 mL), water (1×500 mL) and then with saturated sodium chloride solution (1×500 mL).

The organic phase is dried over sodium sulphate, filtered and then evaporated.

The crude oil obtained is purified by fractional distillation under reduced pressure (100° C./2×10$^{-2}$ mmHg).

Step B: tert-Butyl 2-oxo-cyclopentanecarboxylate tert-Butanol (5.66 mL; 0.06 mole—0.05 eq.) and also 14 g of di-tert-butyl adipate are poured, at ambient temperature, into a suspension of NaH (108.54 g of 60% substance; 2.71 moles—2.15 eq.) in 1.1 L of anhydrous toluene. The reaction mixture is heated at reflux. At that temperature, a solution of di-tert-butyl adipate (324.6 g; 1.26 moles) dissolved in 500 mL of anhydrous toluene is poured in dropwise, whilst controlling the evolution of gas.

Approximate duration of the addition: 3 hours.

Note: substantial clumping of the reaction mixture will be observed in the course of adding the di-tert-butyl adipate but this will develop towards a suspension.

Once the addition is complete, the reaction mixture is held at reflux for 5 hours.

After cooling, the reaction mixture is hydrolysed, at 0° C., using 10% acetic acid solution (1 L). The organic phase is separated off, and the aqueous phase is extracted with toluene (300 ml). The combined toluene phases are washed with water (2×300 ml) and then with saturated sodium chloride solution (300 ml).

The organic phase is dried over sodium sulphate, filtered and then evaporated.

The orange oil is purified by fractional distillation under reduced pressure (65-70° C./1×10$^{-1}$ mmHg).

Step C: tert-Butyl (1S)-2-oxo-1-(3-oxopropyl)cyclopentanecarboxylate

A solution of acrolein (4.19 g; 74.83 mmoles—2.5 eq.) in 10 mL of anhydrous dichloromethane is poured, over 30 minutes, at −25° C., under argon and with slow stirring, into a solution of tert-butyl 2-oxo-cyclopentanecarboxylate (5.51 g; 29.93 mmoles) and catalyst Q (1.46 g; 2.99 mmoles—0.1 eq.) in 60 mL of anhydrous dichloromethane

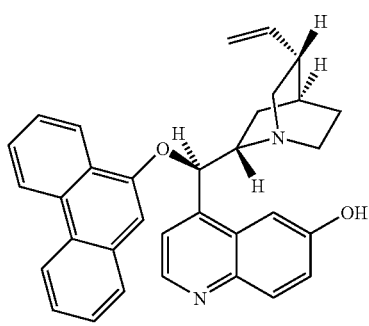

catalyst Q - synthesis described in
*Angew. Chem. Int. Ed.* 2005, 44, 105-108

At the end of the addition, the reaction mixture is stirred for four hours at that temperature and then overnight at −5° C. The filtrate is evaporated to yield a colourless oil.

Step D: tert-Butyl (1S)-1-(3-hydroxypropyl)-2-oxo-cyclopentanecarboxylate

To a solution of the keto ester aldehyde from the Step above (6.5 g; 26.9 mmoles) in 80 mL of anhydrous tetrahydrofuran there is added sodium triacetoxyborohydride (6.84 g; 32.3 mmoles—1.2 eq.). The reaction mixture is heated at reflux, with stirring, for 5 hours 30 minutes. After returning to ambient temperature, the reaction mixture is evaporated. The residue is taken up in 100 mL of $CH_2Cl_2$ and washed with saturated sodium bicarbonate solution (2×20 mL). The basic aqueous phase is extracted with $CH_2Cl_2$. The combined organic phases are washed with saturated sodium chloride solution, dried over sodium sulphate and then evaporated. The crude product is purified by flash chromatography on silica gel using a mixture of $CH_2Cl_2$/isopropanol (95/5) as eluant.

Step E: tert-Butyl (1S)-1-(3-bromopropyl)-2-oxocyclopentanecarboxylate

To a solution of the alcohol from the Step above (5.4 g; 22.12 mmoles) and triphenylphosphine (6.7 g; 25.44 mmoles—1.15 eq.) in 35 mL of anhydrous dichloromethane there is added N-bromosuccinimide (4.53 g; 25.44 mmoles—1.15 eq.) in portions, whilst holding the temperature at 5° C. After stirring for 1 hour at ambient temperature, the reaction mixture is evaporated. The residue is taken up in 100 mL of isopropyl ether and triturated to obtain crystallisation of triphenylphosphine oxide. The solid is filtered off and rinsed. The filtrate is concentrated, then taken up in pentane and then filtered again. The pentane-containing filtrate is evaporated. The crude product is filtered by flash chromatography on silica gel using a mixture of heptane/ethyl acetate (8/2) as eluant.

Step F: tert-Butyl (1S,2R)-1-(3-bromopropyl)-2-hydroxycyclopentanecarboxylate At ambient temperature, with stirring, a commercially available 1.8M solution of (+)DIPCl in hexane (320 mL; 0.577 mole—1.5 eq.) is poured onto the keto ester (117.5 g; 0.385 mole) obtained in the course of the Step above. The reaction mixture is stirred at 55° C. overnight at ambient temperature.

To the reaction mixture there are added 950 mL of ethyl ether and then, with stirring, at 0° C., acetaldehyde (35.9 mL; 0.635 mole—9.65 eq.). The reaction mixture is stirred at ambient temperature for 4 hours. After cooling the reaction mixture to 10° C., 6N sodium hydroxide solution (480 mL; 2.88 moles—7.5 eq.) is added. The reaction mixture is stirred at ambient temperature for 1 hour. The organic phase is separated off, washed with water (3×300 ml), 10% citric acid solution (2×300 mL) and then saturated sodium chloride solution (3×150 mL). The organic phase is dried over sodium sulphate and then evaporated. The crude product is purified by flash chromatography on silica gel using a gradient of heptane/ethyl acetate (95/5 to 85/15) as eluant.

Step G: tert-Butyl(1S,2R)-1-{3-[bis(tert-butoxycarbonyl)amino]propyl}-hydroxycyclopentane-carboxylate To a solution of the brominated alcohol from the Step above (11.8 g; 36.06 mmoles) in 110 mL of anhydrous DMF there are added, at ambient temperature, di-tert-butyl iminodicarboxylate (7.83 g; 36.06 mmoles; 1 eq.) and then caesium carbonate (11.75 g; 36.06 mmoles; 1 eq.). The reaction mixture is stirred at ambient temperature for 3 hours.

The reaction mixture is filtered. After concentrating the filtrate, the oily residue is taken up in 300 mL of ethyl acetate. The ethyl acetate phase is washed with water (3×100 mL) and then with saturated sodium chloride solution (100 mL). The organic phase is dried over sodium sulphate, filtered and evaporated.

The crude product is purified by flash chromatography on silica gel using a gradient of heptane/ethyl acetate (9/1 to 85/15) as eluant.

Step H: tert-Butyl (1S,2R)-1-{3-[bis(tert-butoxycarbonyl)amino]propyl}-2-[(methylsulphonyl)-oxy]cyclopentanecarboxylate Triethylamine (4.11 mL; 29.55 mmoles; 1.5 eq.) is added, at ambient temperature, to a solution of the alcohol from the Step above (8.70 g; 19.7 mmoles) in 130 mL of anhydrous tetrahydrofuran. The reaction mixture is cooled to −30° C. and there is then poured in, dropwise, mesyl chloride (2.29 mL; 29.55 mmoles; 1.5 eq.) dissolved in 10 mL of anhydrous tetrahydrofuran. The mixture is allowed to come back up to, and is stirred at, ambient temperature for two hours. After evaporating off the tetrahydrofuran, the reaction mixture is taken up in 200 mL of ethyl acetate. The ethyl acetate phase is washed with water (2×20 mL) and then with saturated sodium chloride solution (1×20 mL). The organic phase is dried over sodium sulphate, filtered and then evaporated.

The crude product is purified by flash chromatography on silica gel using a gradient of heptane/ethyl acetate (85/15 to 8/2) as eluant.

Step I: tert-Butyl (1R,2S)-2-(acetylthio)-{3-[bis(tert-butoxycarbonyl)amino]propyl}-cyclopentanecarboxylate The expected product is obtained, starting from the compound obtained in the Step above, in accordance with the procedure of Step G of Example 1.

Step J: (1R,2S)-1-(3-Aminopropyl)-2-mercaptocyclopentanecarboxylic acid hydrochloride Deprotection of the Acid and Amine Functions:
To a solution of the compound obtained in the Step above (8.80 g; 17.6 mmoles) in 100 mL of anhydrous $CH_2Cl_2$ there is added dropwise, at ambient temperature, 4M HCl/dioxane solution (132 mL; 0.53 moles; 30 eq.). The reaction mixture is left at ambient temperature, with stirring, until the two functions have been deprotected (checked by LC/MS—approximate duration: overnight) and the solvents are then evaporated off. The product obtained is used without purification in the next step.

Deprotection of the Thiol:
The evaporation product is taken up in 200 mL of 4M aqueous HCl solution previously degassed with argon and is then heated at 45° C. overnight. After cooling, the reaction mixture is diluted with 100 mL of degassed water and is then lyophilised.

Step K: (1R,2S)-1-(3-Aminopropyl)-2-mercaptocyclopentanecarboxylic acid

The compound of the Step above (10 g, 41.5 mmol) is dissolved in 80 mL of water and stirred. The solution is a clear pale yellow (pH: about 1.2). Whilst stirring, about 11 mL of saturated sodium bicarbonate solution are added. From pH=4, there is observed a first precipitate which is filtered off. The filtrate is then rendered more basic, up to pH=5.5, filtering off the precipitates as and when they are formed. The filtrate is evaporated under reduced pressure (Tbath=55° C.). When about 10 mL of solution remain, filtration is carried out again.

The precipitates of equivalent quality are collected and dried in vacuo to yield the title product.

NMR Spectroscopy:
($^1$H NMR, $D_2O$, 600 MHz) δ=3.08 ppm (1H, dd); 2.91 (2H, t); 2.18 (1H, m); 2.11 (1H, m); 1.79 (1H, m); 1.69-1.56 (4H, m); 1.52 (1H, m); 1.45 (1H, m); 1.37 (1H, m).

EXAMPLE 3b (1R,2S)-1-(3-Aminopropyl)-2-mercaptocyclopentanecarboxylic acid phosphate The compound of Example 3a is reacted with phosphoric acid 85% in water and then lyophilised.
NMR Spectroscopy:
($^1$H NMR, $D_2O$, 600 MHz) δ=3.09 ppm (1H, t); 2.93 (2H, t); 2.18 (2H, m); 1.82 (1H, m); 1.79 (1H, dt); 1.72-1.50 (5H, m); 1.41 (1H, dt).

EXAMPLE 3c (1R,2S)-1-(3-Aminopropyl)-2-mercaptocyclopentanecarboxylic acid besylate The compound of Example 3a is reacted with benzenesulphonic acid in water and is then lyophilised.

NMR Spectroscopy:
($^1$H NMR, DMSO-D6, 600 MHz) δ=12.38 ppm (1H, sl); 7.64 (3H, sl); 7.59 (2H, m); 7.32 (2H, m); 7.29 (1H, m); 3.02 (1H, tl); 2.76 (2H, m); 2.33 (1H, sl); 2.13 (2H, m); 1.84-1.65 (3H, m); 1.61 (1H, m); 1.52 (3H, m); 1.32 (1H, m).

EXAMPLE 4

(1S,2R)-1-(3-Aminopropyl)-2-mercaptocyclopentanecarboxylic acid trifluoroacetate The expected product is obtained in accordance with the procedure described in Steps I and J of Example 1, starting from the other enantiomer obtained in Step H of Example 1, that is to say benzyl(1S,2R)-2-(acetylthio)-1-(3-{[(benzyloxy)carbonyl]amino}propyl)cyclopentane-carboxylate.
CAD/MS/MS spectrum of [M+H]$^+$=204.1 in accordance with the expected structure

EXAMPLE 5

(1S,2R)-2-Acetylthio-1-(3-aminopropyl)-cyclopentanecarboxylic acid hydrochloride The expected product is obtained in accordance with the procedure described for Example 2, starting from the other enantiomer obtained in Step H of Example 1, that is to say benzyl (1S,2R)-2-(acetylthio)-1-(3-{[(benzyloxy)carbonyl]amino}propyl)cyclopentanecarboxylate.

| Elemental microanalysis | C | H | N | S | Cl- |
|---|---|---|---|---|---|
| Calculated % | 46.88 | 7.15 | 4.97 | 11.38 | 12.58 |
| Found % | 46.90 | 7.25 | 5.02 | 11.09 | 12.78 |

EXAMPLE 6

1-(3-Aminopropyl)-2-mercaptocyclopentanecarboxylic acid trifluoroacetate (racemic cis diastereoisomer)

The expected product is obtained in accordance with the procedure described in Steps I and J of Example 1, starting from the compound obtained in Step G of Example 1.
CAD/MS/MS spectrum of [M+H]$^+$=204.1 in accordance with the expected structure.

EXAMPLE 7

1-(4-Aminobutyl)-2-mercaptocyclopentanecarboxylic acid trifluoroacetate (racemic trans diastereoisomer)

Step A: Benzyl 1-(4-bromobutyl)-2-oxo-cyclopentanecarboxylate

In a 500 mL three-necked flask provided with magnetic stirring and a condenser, under an inert nitrogen atmosphere, sodium hydride 95% (2.2 g; 87.1 mmol; 1.25 eq.) is suspended in a mixture of anhydrous THF (115 mL) and HMPA (14.6 mL). A solution of benzyl 2-oxocyclopentanecarboxylate (15.3 g; 70.3 mmol) in 45 mL of anhydrous THF is added dropwise so as to keep the temperature below 45° C. The reaction mixture is stirred for 1 hour at ambient temperature. 1,4-Dibromobutane (12.6 mL; 105.4 mmol; 1.5 eq.) is added to the clear yellow solution. The reaction mixture is stirred again, for 14 hours, at reflux. After coming back to ambient temperature, 80 mL of saturated aqueous ammonium chloride solution are added. The mixture is poured into 500 mL of ether and the organic phase is washed five times with 100 mL of water and then with 100 mL of saturated aqueous sodium chloride solution. The organic phase is dried over MgSO$_4$, filtered and concentrated.

The product is purified on silica gel using a mixture of cyclohexane/ethyl acetate (gradient 95/5 to 80/20) as eluant to yield the expected product in the form of a yellow oil.

Step B: Benzyl 1-(4-bromobutyl)-2-hydroxy-cyclopentanecarboxylate

The expected product is obtained in accordance with the procedure described in Step E of Example 1, starting from the compound obtained in the Step above.

Step C: Benzyl 1-(4-azidobutyl)-2-hydroxy-cyclopentanecarboxylate

In a flask, under an inert nitrogen atmosphere, the compound obtained in the Step above (4.41 g; 16.6 mmol), sodium azide (5.5 g; 84.6 mmol; 5 eq.) and sodium iodide (0.2 g) are suspended in 60 mL of ethanol. The reaction mixture is stirred at reflux for 24 hours and is then concentrated to dryness. The oily residue is dissolved in 150 mL of ether and 80 mL of water. The organic phase is washed with 80 mL of water and 40 mL of saturated aqueous sodium chloride solution. The organic phase is dried over MgSO$_4$, filtered and concentrated.

The (Rac)-trans and (Rac)-cis azide mixture formed is used as such in the next reaction.

Step D: Benzyl 1-(4-aminobutyl)-2-hydroxy-cyclopentanecarboxylate

In a flask, the (Rac)-trans and (Rac)-cis azide mixture (20.64 g; 62.3 mmol) and triphenylphosphine (24.4 g; 93 mmol; 1.5 eq.) are dissolved in 500 mL of THF. The solution is stirred for 1 hour at 50° C. Water (10 mL; 556 mmol; 9 eq.) is added. The reaction mixture is stirred for 4 hours at 50° C. and is then concentrated to dryness. The oily residue is dissolved in 250 mL of ether and the organic phase is extracted twice with 120 mL of 1N aqueous hydrochloric acid solution. The aqueous phase is washed with 100 mL of ether. The pH of the aqueous phase is brought to 12-13 by adding solid potassium hydroxide. The aqueous phase is extracted 3 times with 250 mL of ethyl acetate. The combined organic phases are washed with 100 mL of water and then with 100 mL of saturated aqueous sodium chloride solution. The organic phase is dried over MgSO$_4$, filtered and concentrated.

The expected product, obtained in the form of a cis/trans mixture, is used as such in the next reaction.

Step E: Benzyl 1-(4-{[benzyloxy)carbonyl]amino}butyl)-2-hydroxy-cyclopentanecarboxylate In a flask, the product obtained in the Step above (62.3 mmol) is dissolved in 160 mL of dioxane. An aqueous solution of sodium carbonate (13.16 g; 124 mmol; 2 eq.) in 160 mL of water is added. At 0° C., slowly add a solution of benzyl chloroformate (12 mL; 84.4 mmol; 1.35 eq.) in 30 mL of dioxane. The reaction mixture is stirred at ambient temperature for 12 hours and is then partly concentrated. The aqueous phase is extracted twice with 250 mL of ether. The combined organic phases are washed, dried, filtered and concentrated.

The product is purified on silica gel (petroleum ether/ethyl acetate:gradient of 9/1 to 2/8) to yield the expected product in the form of a yellow oil.

Step F: Benzyl 1-(4-{[benzyloxy)carbonyl]amino}butyl)-2-[(methylsulphonyl)oxy-cyclopentanecarboxylate (racemic cis diastereoisomer)

The expected product is obtained in accordance with the procedure described in Step F of Example 1, starting from the compound obtained in the Step above.

The cis diastereoisomer is the first in the order of elution.

Step G: Benzyl 2-(acetylthio)-1-(4-{[benzyloxy)carbonyl]amino}butyl)-cyclopentanecarboxylate (racemic trans diastereoisomer)

The expected product is obtained in accordance with the procedure described in Step G of Example 1, starting from the cis compound obtained in the Step above.

Step H: 1-(4-Aminobutyl)-2-mercaptocyclopentanecarboxylic acid trifluoroacetate (racemic trans diastereoisomer)

The expected product is obtained in accordance with the procedure described in Steps I and J of Example 1, starting from the compound obtained in the Step above.

| Elemental microanalysis | C | H | N | S |
|---|---|---|---|---|
| Calculated % | 43.5 | 6.08 | 4.23 | 9.68 |
| Found % | 43.9 | 6.24 | 4.22 | 9.59 |

EXAMPLE 8

1-(4-Aminobutyl)-2-mercaptocyclopentanecarboxylic acid trifluoroacetate (racemic cis diastereoisomer)

Step A: Benzyl 1-(4-{[benzyloxy)carbonyl]amino}butyl)-2-[(methylsulphonyl)oxy-cyclopentanecarboxylate (racemic trans diastereoisomer)

The expected product is the other diastereoisomer obtained in Step F of Example 7 (trans diastereoisomer).

Step B: 1-(4-Aminobutyl)-2-mercaptocyclopentanecarboxylic acid trifluoroacetate (racemic cis diastereoisomer)

The expected product is obtained in accordance with the procedure described in Steps G, I and J of Example 1, starting from the compound obtained in the Step above.

| Elemental microanalysis | C | H | N | S |
|---|---|---|---|---|
| Calculated % | 43.5 | 6.08 | 4.23 | 9.68 |
| Found % | 43.56 | 6.26 | 4.13 | 9.36 |

EXAMPLE 9

1-(4-Aminobutyl)-2-mercaptocyclopentanecarboxylic acid trifluoroacetate (cis diastereoisomer, enantiomer 1)

Step A: Benzyl 2-(acetylthio)-1-(4-{[benzyloxy)carbonyl]amino}butyl)-cyclopentanecarboxylate (cis diastereoisomer, enantiomer 1)

The expected product is obtained in accordance with the procedure described in Steps G and H of Example 1, starting from the compound obtained in Step A of Example 8.
Enantiomer 1 is the first in the order of elution.

Step B:
1-(4-Aminobutyl)-2-mercaptocyclopentanecarboxylic acid trifluoroacetate (cis diastereoisomer, enantiomer 1)

The expected product is obtained in accordance with the procedure described in Steps I and J of Example 1, starting from the compound obtained in the Step above.
CAD/MS/MS spectrum of $[M+H]^+=218$ in accordance with the expected structure.

EXAMPLE 10

1-(4-Aminobutyl)-2-mercaptocyclopentanecarboxylic acid trifluoroacetate (cis diastereoisomer, enantiomer 2)

Step A: Benzyl 2-(acetylthio)-1-(4-{[benzyloxy)carbonyl]amino}butyl)-cyclopentanecarboxylate (cis diastereoisomer, enantiomer 2)

The expected product is the other enantiomer obtained in Step A of Example 9.

Step B:
1-(4-Aminobutyl)-2-mercaptocyclopentanecarboxylic acid trifluoroacetate (cis diastereoisomer, enantiomer 2)

The expected product is obtained in accordance with the procedure described in Steps I and J of Example 1, starting from the compound obtained in the Step above.
CAD/MS/MS spectrum of $[M+H]^+=218$ in accordance with the expected structure

EXAMPLE 11

1-[(4-Aminomethyl)benzyl]-2-mercaptocyclopentanecarboxylic acid trifluoroacetate (racemic cis diastereoisomer)

Step A: Benzyl 1-(4-bromomethyl)benzyl]-2-oxo-cyclopentanecarboxylate

The expected product is obtained in accordance with the procedure described in Step A of Example 7, starting from benzyl 2-oxo-cyclopentanecarboxylate and 1,4-dibromomethylbenzene.

Step B: Benzyl 1-(4-bromomethyl)benzyl]-2-hydroxy-cyclopentanecarboxylate (racemic trans diastereoisomer)

The expected product is obtained in accordance with the procedure described in Step E of Example 1, followed by diastereoisomeric separation of the compound thereby obtained, by flash chromatography on silica gel using a mixture of cyclohexane/ethyl acetate (gradient of 90/10 to 65/35) as eluant.
The trans diastereoisomer is the first in the order of elution.

Step C: 1-[(4-Aminomethyl)benzyl]-2-mercaptocyclopentanecarboxylic acid trifluoroacetate (racemic cis diastereoisomer)

The expected product is obtained in accordance with the procedure described in Steps C to H of Example 7, starting from the compound obtained in the Step above.
CAD/MS/MS spectrum of $[M+H]^+=266.1$ in accordance with the expected structure

EXAMPLE 12

2-Mercapto-1(piperidin-4-ylmethyl)-cyclopentanecarboxylic acid trifluoroacetate (racemic trans diastereoisomer)

Step A: Benzyl 4-({1-[(benzyloxy)carbonyl]-2-hydroxy-cyclopentyl}methyl)-1-piperidinecarboxylate (racemic cis diastereoisomer)

The expected product is obtained in accordance with the procedure described in Steps A and B of Example 7, starting from benzyl 2-oxo-cyclopentanecarboxylate and benzyl 4-bromomethyl-1-piperidinecarboxylate.
The cis diastereoisomer is the second in the order of elution.

Step B: Benzyl 4-({1-[(benzyloxy)carbonyl]-2-[(methylsulphonyl)oxy]cyclopentyl}methyl)-1-piperidinecarboxylate (racemic cis diastereoisomer)

The expected product is obtained in accordance with the procedure described in Step F of Example 1, starting from the compound obtained in the Step above.

Step C: 2-Mercapto-1-(piperidin-4-ylmethyl)-cyclopentanecarboxylic acid trifluoroacetate (racemic trans diastereoisomer)

The expected product is obtained in accordance with the procedure described in Steps G, I and J of Example 1, starting from the compound obtained in the Step above.

| Elemental microanalysis | C | H | N | S |
|---|---|---|---|---|
| Calculated % | 47.05 | 6.2 | 3.92 | 8.97 |
| Found % | 47.12 | 6.52 | 4.03 | 7.6 |

EXAMPLE 13

2-Mercapto-1-(piperidin-4-ylmethyl)-cyclopentanecarboxylic acid trifluoroacetate (racemic cis diastereoisomer)

Step A: Benzyl 4-({1-[(benzyloxy)carbonyl]-2-[(methylsulphonyl)oxy]cyclopentyl}methyl)-1-piperidinecarboxylate (racemic trans diastereoisomer)

The expected product is the other diastereoisomer obtained in Step B of Example 12 (trans diastereoisomer).

Step B: 2-Mercapto-1-(piperidin-4-ylmethyl)-cyclopentanecarboxylic acid trifluoroacetate (racemic cis diastereoisomer)

The expected product is obtained in accordance with the procedure described in Steps G, I and J of Example 1, starting from the compound obtained in the Step above.

| Elemental microanalysis | C | H | N | S |
|---|---|---|---|---|
| Calculated % | 47.05 | 6.2 | 3.92 | 8.97 |
| Found % | 46.58 | 6.24 | 4.02 | 7.78 |

EXAMPLE 14

1-(5-Aminopentyl)-2-mercaptocyclopentanecarboxylic acid trifluoroacetate (racemic trans diastereoisomer)

Step A: Benzyl 1-(5-{[benzyloxy)carbonyl]amino}pentyl)-2-hydroxy-cyclopentanecarboxylate The expected product is obtained in accordance with the procedure described in Steps A to E of Example 7, starting from benzyl 2-oxo-cyclopentanecarboxylate and 1,5-dibromopentane.

Step B: Benzyl 1-(5-{[benzyloxy)carbonyl]amino}pentyl)-2-[(methylsulphonyl)oxy-cyclopentanecarboxylate (racemic cis diastereoisomer)

The expected product is obtained in accordance with the procedure described in Step F of Example 1, starting from the compound obtained in the Step above. The cis diastereoisomer is the second in the order of elution.

Step C: 1-(5-Aminopentyl)-2-mercaptocyclopentanecarboxylic acid trifluoroacetate (racemic trans diastereoisomer)

The expected product is obtained in accordance with the procedure described in Steps G, I and J of Example 1, starting from the compound obtained in the Step above.
CAD/MS/MS spectrum of $[M+H]^+=232.1$ in accordance with the expected structure

EXAMPLE 15

1-(5-Aminopentyl)-2-mercaptocyclopentanecarboxylic acid trifluoroacetate (racemic cis diastereoisomer)

Step A: Benzyl 1-(5-{[benzyloxy)carbonyl]amino}pentyl)-2-[(methylsulphonyl)oxy-cyclopentanecarboxylate (racemic trans diastereoisomer)

The expected product is the other diastereoisomer obtained in Step B of Example 14 (trans diastereoisomer).

Step B: 1-(5-Aminopentyl)-2-mercaptocyclopentanecarboxylic acid trifluoroacetate (racemic cis diastereoisomer)

The expected product is obtained in accordance with the procedure described in Steps G, I and J of Example 1, starting from the compound obtained in the Step above.

| Elemental microanalysis | C | H | N | S |
|---|---|---|---|---|
| Calculated % | 45.21 | 6.42 | 4.06 | 9.28 |
| Found % | 45.41 | 6.76 | 4.1 | 9.75 |

EXAMPLE 16

2-Mercapto-1-(2-piperidin-4-ylethyl)-cyclopentanecarboxylic acid trifluoroacetate (racemic cis diastereoisomer)

Step A: Benzyl 4-(2-{1-[(benzyloxy)carbonyl]-2-hydroxy-cyclopentyl}ethyl)-1-piperidine-carboxylate The expected product is obtained in accordance with the procedure described in Steps A and B of Example 7, starting from benzyl 2-oxo-cyclopentanecarboxylate and benzyl 4-(2-bromoethyl)-1-piperidinecarboxylate.
The trans diastereoisomer is the first in the order of elution.

Step B: Benzyl 4-(2-{1-[(benzyloxy)carbonyl]-2-[(methylsulphonyl)oxy]cyclopentyl}ethyl)-1-piperidinecarboxylate (racemic trans diastereoisomer)

The expected product is obtained in accordance with the procedure described in Step F of Example 1, starting from the compound obtained in the Step above.

Step C: 2-Mercapto-1-(2-piperidin-4-ylethyl)-cyclopentanecarboxylic acid trifluoroacetate (racemic cis diastereoisomer)

The expected product is obtained in accordance with the procedure described in Steps G, I and J of Example 1, starting from the compound obtained in the Step above.
CAD/MS/MS spectrum of $[M+H]^+=258$ in accordance with the expected structure

EXAMPLE 17

2-Mercapto-1-(pyridin-3-ylmethyl)-cyclopentanecarboxylic acid trifluoroacetate (racemic cis diastereoisomer)

Step A: Benzyl 2-oxo-1-(3-pyridylmethyl)cyclopentanecarboxylate

In a 1-liter three-necked flask provided with magnetic stirring and a condenser, under an inert nitrogen atmosphere, potassium hydride 32% (25 g; 200 mmoles; 1.1 eq.) is suspended in anhydrous THF (200 mL). The reaction mixture is cooled to −78° C. and then benzyl 2-oxocyclopentanecarboxylate (39.7 g; 182 mmoles) is added dropwise whilst keeping the temperature below −78° C. The reaction mixture is stirred for 1 hour at ambient temperature. A solution of 3-(chloromethyl)-pyridine base (38.7 g; 226 mmoles; 1.24 eq.) in 100 mL of anhydrous THF is added to the clear yellow solution. The reaction mixture is stirred at reflux for 12 hours. After coming back to ambient temperature, the reaction mixture is evaporated to dryness and taken up in 80 mL of water and 500 mL of ethyl acetate. The aqueous phase is extracted three times with 50 mL of ethyl acetate. The combined organic phases are washed with saturated sodium chloride solution and then dried over $MgSO_4$, filtered and concentrated. The product is purified on silica gel using a mixture of dichloromethane/ethanol (gradient of 98/2 to 95/5) as eluant to yield the expected product in the form of a yellow oil.

Step B: Benzyl 2-hydroxy-1-(3-pyridylmethyl)cyclopentanecarboxylate (racemic trans diastereoisomer)

The expected product is obtained in accordance with the procedure described in Step E of Example 1.

The product is purified on silica gel using a mixture of dichloromethane/ethyl acetate (gradient of 7/3 to 5/5) as eluant to yield the expected product in the form of a colourless oil.

The trans diastereoisomer is the second in the order of elution.

Step C: 2-Mercapto-1-(pyridin-3-ylmethyl)-cyclopentanecarboxylic acid trifluoroacetate (racemic cis diastereoisomer)

The expected product is obtained in accordance with the procedure described in Steps F, G, I and J of Example 1, starting from the compound obtained in the Step above.

| Elemental microanalysis | C | H | N | S |
|---|---|---|---|---|
| Calculated % | 47.86 | 4.59 | 3.99 | 9.13 |
| Found % | 45.85 | 4.93 | 3.85 | 7.26 |

CAD/MS/MS spectrum of $[M+H]^+=238.1$ in accordance with the expected structure

EXAMPLE 18

2-Mercapto-1-(2-pyridin-2-ylethyl)-cyclopentanecarboxylic acid trifluoroacetate (racemic cis diastereoisomer)

Step A: Benzyl 2-oxo-1-(2-pyridin-2-ylethyl)cyclopentanecarboxylate

The expected product is obtained in accordance with the procedure described in Step A of Example 17, starting from benzyl 2-oxo-cyclopentanecarboxylate and 2-pyridin-2-ylethanyl methanesulphonate.

Step B: Benzyl 2-hydroxy-1-(2-pyridin-2-ylethyl)cyclopentanecarboxylate (racemic trans diastereoisomer)

The expected product is obtained in accordance with the procedure described in Step B of Example 17.

The trans diastereoisomer is the second in the order of elution.

Step C: 2-Mercapto-1-(2-pyridin-2-ylethyl)-cyclopentanecarboxylic acid trifluoroacetate (racemic cis diastereoisomer)

The expected product is obtained in accordance with the procedure described in Steps F, G, I and J of Example 1, starting from the compound obtained in the Step above.

| Elemental microanalysis | C | H | N | S |
|---|---|---|---|---|
| Calculated % | 49.31 | 4.97 | 3.83 | 8.78 |
| Found % | 45.54 | 5.11 | 3.48 | 7.56 |

CAD/MS/MS spectrum of $[M+H]^+=252.1$ in accordance with the expected structure

EXAMPLE 19

1-[(6-Aminopyridin-3-ylmethyl)]-2-mercaptocyclopentanecarboxylic acid trifluoroacetate (racemic cis diastereoisomer)

Step A: tert-Butyl 2-oxo-cyclopentanecarboxylate

1) Di-tert-butyl adipate

Adipoyl chloride (629.8 g; 3.44 moles) is poured dropwise, at ambient temperature, into a solution of tert-butanol (3.27 L; 34.4 moles—10 eq.) and pyridine (800 mL; 10.32 moles—3 eq.) in 3 L of anhydrous toluene. The reaction mixture is heated at 70° C., with stirring, overnight. After cooling, the precipitate of pyridinium chloride is filtered off and rinsed with toluene. The toluene phase is washed with 1N hydrochloric acid solution (4×500 mL), 10% sodium carbonate solution (1×500 mL), water (1×500 mL) and then with saturated sodium chloride solution (1×500 mL).

The organic phase is dried, filtered and then evaporated.

The crude oil obtained is purified by fractional distillation under reduced pressure (100° C./2×10$^{-2}$ mmHg).

2) tert-Butyl 2-oxo-cyclopentanecarboxylate tert-Butanol (5.66 mL; 0.06 mole—0.05 eq.) and also 14 g of di-tert-butyl adipate are poured, at ambient temperature, into a suspension of NaH (108.54 g of 60% substance; 2.71 moles—2.15 eq.) in 1.1 L of anhydrous toluene. The reaction mixture is heated at reflux. At that temperature, a solution of di-tert-butyl adipate (324.6 g; 1.26 moles) dissolved in 500 mL of anhydrous toluene is poured in dropwise, whilst controlling the evolution of gas.

Approximate duration of the addition: 3 hours.

Note: substantial clumping of the reaction mixture will be observed in the course of adding the di-tert-butyl adipate but this will develop towards a suspension.

Once the addition is complete, the reaction mixture is held at reflux for 5 hours.

After cooling, the reaction mixture is hydrolysed, at 0° C., using 10% acetic acid solution (1 L). The organic phase is separated off, and the aqueous phase is extracted with toluene (300 ml). The combined toluene phases are washed with water (2×300 ml) and then with saturated sodium chloride solution (300 ml).

The organic phase is dried over sodium sulphate, filtered and then evaporated.

The orange oil is purified by fractional distillation under reduced pressure (65-70° C./1×10$^{-1}$ mmHg).

Step B: tert-Butyl 1-({6-[(tert-butoxycarbonyl)amino]-3-pyridyl}methyl)-2-oxocyclopentanecarboxylate The expected product is obtained in accordance with the procedure described in Step A of Example 17, starting from tert-butyl 2-oxo-cyclopentanecarboxylate and tert-butyl[5-(chloromethyl)pyridin-2-yl]carbamate.

Step C: tert-Butyl 1-({6-[(tert-butoxycarbonyl)amino]-3-pyridyl}methyl)-2-hydroxy-cyclopentanecarboxylate The expected product is obtained in accordance with the procedure described in Step B of Example 17.

The product is purified on silica gel using a mixture of dichloromethane/ethanol (gradient of 98/2 to 95/5) to yield the expected product in the form of a colourless oil.

The trans diastereoisomer is the second in the order of elution.

Step D: tert-Butyl 1-({6-[(tert-butoxycarbonyl)amino]-3-pyridyl}methyl)-2-[(methyl-sulphonyl)oxy]-cyclopentanecarboxylate (racemic trans diastereoisomer)

The expected product is obtained in accordance with the procedure described in Step F of Example 1, starting from the compound obtained in the Step above.

Step E: 1-[(6-Aminopyridin-3-ylmethyl)]-2-(acetylthio)-cyclopentanecarboxylic acid (racemic cis diastereoisomer)

The expected product is obtained in accordance with the procedure described in Step G of Example 1, starting from the compound obtained in the Step above.

Step F: 1-[(6-Aminopyridin-3-ylmethyl)]-2-mercaptocyclopentanecarboxylic acid trifluoroacetate (racemic cis diastereoisomer)

Deprotection of the Acid and Amine Functions:

To a solution of the compound obtained in the Step above (2.40 g; 4.72 mmoles) in 20 mL of anhydrous $CH_2Cl_2$ there is added dropwise, at ambient temperature, 4M HCl/dioxane solution (35.5 mL; 141.6 mmoles; 30 eq.). The reaction mixture is left at ambient temperature, with stirring, until the two (amine and acid) functions have been deprotected (checked by LC/MS—approximate duration: overnight) and the solvents are then evaporated off Deprotection of the Thiol:

The evaporation product is taken up in 4M aqueous HCl solution and is then heated at 45° C. overnight. The reaction mixture is diluted with water and then lyophilised.

The product is purified on BIOGEL P2 using a mixture of water/acetonitrile (1/1) as eluant. The fractions containing the expected product are lyophilised.

CAD/MS/MS spectrum of $[M+H]^+=253.1$ in accordance with the expected structure

EXAMPLE 20

(1R,2S,1'R,2'S)-2,2'-Disulphanediylbis[1-(3-aminopropyl)cyclopentane-carboxylic acid]dihydrochloride A solution of the compound described in Step J of Example 1 (0.44 g; 1.39 mmoles) in 3 mL of 1N sodium hydroxide is heated at 65° C. overnight. After cooling, the reaction mixture is neutralised with 3 mL of 1N hydrochloric acid solution.

The product is purified on BIOGEL P2 using a mixture of water/acetonitrile (1/1) as eluant. The fractions containing the expected product are lyophilised.

| Elemental microanalysis | C | H | N | S | Cl– |
|---|---|---|---|---|---|
| Calculated % | 45.28 | 7.18 | 5.87 | 13.43 | 14.85 |
| Found % | 45.31 | 6.83 | 5.94 | 13.32 | 14.54 |

EXAMPLE 21

(1R,2S)-1-[3-(Dimethylamino)propyl]-2-mercapto-cyclopentanecarboxylic acid trifluoroacetate Step A: (1R,2S,1'R,2'S)-2,2'-Disulphanediylbis[1-(3-(dimethylamino)propyl)cyclopentane-carboxylic acid To a solution of the compound obtained in Example 20 (0.57 g; 0.70 mmole) in 4.5 mL of formic acid there is added dropwise, at ambient temperature, 0.2 mL of 37% aqueous formaldehyde solution. The reaction mixture is heated at reflux, with stirring, for one hour. After cooling, the reaction mixture is diluted with 10 mL of water and then the solvents are evaporated off. The product is used without purification in the next Step.

Step B: (1R,2S)-1-[3-(Dimethylamino)propyl]-2-mercaptocyclopentanecarboxylic acid trifluoroacetate To a solution of the compound obtained in the Step above in 35 mL of a mixture of water/THF (1/1), there are added dropwise, at ambient temperature, 2 mL of tributylphosphine. The reaction mixture is heated at 50° C., with stirring, overnight. After cooling, the reaction mixture is diluted with 100 mL of water and the aqueous phase is then washed with ether (3×25 mL). The aqueous phase is evaporated. The crude product is purified by preparative HPLC on a Kromasil column (1 kg–600 mm×60 mm–70 ml/min) using a mixture of water/acetonitrile/trifluoroacetic acid (85/15/0.1) as mobile phase.

The fractions containing the expected product are lyophilised.

CAD/MS/MS spectrum of $[M+H]^+=232.1$ in accordance with the expected structure

EXAMPLE 22

1-[3-(Methylamino)propyl]-2-mercaptocyclopentanecarboxylic acid trifluoroacetate (racemic cis diastereoisomer)

Step A: Benzyl 2-[(methylsulphonyl)oxy]-1-(3-pyridylmethyl)cyclopentanecarboxylate (racemic trans diastereoisomer)

The expected product is obtained in accordance with the procedure described in Steps A, B and C of Example 17, starting from benzyl 2-oxo-cyclopentanecarboxylate and 3-[[benzyloxy)carbonyl](methyl)amino]propyl methanesulphonate.

The trans diastereoisomer is the second in the order of elution.

Step B: 1-[3-(Methylamino)propyl]-2-mercaptocyclopentanecarboxylic acid trifluoroacetate (racemic cis diastereoisomer)

The expected product is obtained in accordance with the procedure described in Steps G, I and J of Example 1, starting from the compound obtained in the Step above. CAD/MS/MS spectrum of $[M+H]^+=218.1$ in accordance with the expected structure

EXAMPLE 23

2-Mercapto-1-(azetidin-3-ylmethyl)-cyclopentanecarboxylic acid trifluoroacetate (racemic cis diastereoisomer)

Step A: Benzyl 3-({1-(tert-butyloxycarbonyl)-2-hydroxy-cyclopentyl}methyl)-1-azetidine-carboxylate The expected product is obtained in accordance with the procedure described in Steps A and B of Example 7, starting from benzyl 2-oxo-cyclopentanecarboxylate and tert-butyl 3-{[(methylsulphonyl)oxy]methyl}azetidine-1-carbamate.

Step B: Benzyl 3-({1-(tert-butyloxycarbonyl)-2-[(methylsulphonyl)oxy]cyclopentyl}methyl)-1-azetidinecarboxylate (racemic trans diastereoisomer)

The expected product is obtained in accordance with the procedure described in Step D of Example 19, starting from the compound obtained in the Step above.

The product is purified on silica gel using a mixture of dichloromethane/ethyl acetate (gradient of 9/1 to 8/2) as eluant to yield the expected product in the form of a colourless oil. The trans diastereoisomer is the second in the order of elution.

Step C: 2-Mercapto-1-(azetidin-3-ylmethyl)-cyclopentanecarboxylic acid trifluoroacetate (racemic cis diastereoisomer)

The expected product is obtained in accordance with the procedure described in Step F of Example 19, starting from the compound obtained in the Step above.

CAD/MS/MS spectrum of $[M+H]^+=216.1$ in accordance with the expected structure

Pharmacological Study

EXAMPLE 24

Inhibition of TAFIa

Purified human TAFI (25 ng) is activated by adding thrombin-thrombomodulin complex in the presence of calcium chloride. After incubating for 20 minutes at 20° C., the reaction is stopped by adding the irreversible thrombin inhibitor PPACK (TAFI Activity Kit, American Diagnostica).

The compound under test is added to the (3.2 nM) TAFIa solution and incubated for 5 minutes at 20° C. A chromogenic TAFIa substrate is added and then incubated for 30 minutes at 37° C. The enzymatic reaction is stopped by adding sulphuric acid (TAFI Activity Kit, American Diagnostica). The optical density (OD) of the solution is measured at 490 nm with the aid of a spectrophotometer (Spectramax, Molecular Devices). The OD value of a well containing the reagents without the TAFI is subtracted from each of the OD values measured. The percentage inhibition of TAFIa at a given concentration of the compound under test is determined using the following formula:

% inhibition=100−[(OD of compound×100)/OD of carrier]

The concentration of compound of the invention which inhibits 50% of the enzymatic activity of TAFIa ($IC_{50}$) is calculated from the inhibition percentages of the OD values measured for increasing concentrations of the compound under test using non-linear regression according to a sigmoidal four-parameter equation (effect-dose). The $IC_{50}$ values obtained with representative compounds of the invention are recorded in nM in the Table below:

| Compound | $IC_{50}$ (nM) |
| --- | --- |
| Example 1 | 6.7 ± 0.6 |
| Example 2 | 22 ± 6 |
| Example 3 | 7.4 ± 1.1 |
| Example 6 | 14 ± 2 |
| Example 8 | 178 ± 11 |
| Example 10 | 81 ± 16 |
| Example 13 | 184 ± 22 |
| Example 20 | 186 ± 26 |

EXAMPLE 25

Pharmaceutical Composition—Tablet

Formula for the preparation of 1000 tablets each containing 10 mg of active ingredient:

| | |
| --- | --- |
| Compound of one of Examples 1 to 23 | 10 g |
| Hydroxypropylcellulose | 2 g |
| Wheat starch | 10 g |
| Lactose | 100 g |
| Magnesium stearate | 3 g |
| Talc | 3 g |

EXAMPLE 26

Pharmaceutical Composition—Tablet, in Association with Warfarin

Formula for the preparation of 1000 tablets each containing 10 mg of active ingredient:

| | |
| --- | --- |
| Compound of one of Examples 1 to 23 | 10 g |
| Warfarin | 2 g |
| Hydroxypropylcellulose | 2 g |
| Wheat starch | 10 g |
| Lactose | 100 g |
| Magnesium stearate | 3 g |
| Talc | 3 g |

EXAMPLE 27

Pharmaceutical Composition—Tablet, in Association with Aspirin

Formula for the preparation of 1000 tablets each containing 10 mg of active ingredient:

| | |
|---|---|
| Compound of one of Examples 1 to 23 | 10 g |
| Aspirin | 100 g |
| Hydroxypropylcellulose | 2 g |
| Wheat starch | 10 g |
| Lactose | 100 g |
| Magnesium stearate | 3 g |
| Talc | 3 g |

EXAMPLE 28

Injectable Solution, in Association with Alteplase

Formula for the preparation of 10 ml of solution:

| | |
|---|---|
| Compound of one of Examples 1 to 23 | 20 mg |
| Alteplase | 10 mg |
| L-Arginine | 350 µg |
| Polysorbate 80 | 1 mg |
| Phosphoric acid | q.s.p. pH 7 |
| Water for injections | 10 ml |

The invention claimed is:

1. A compound of formula (I):

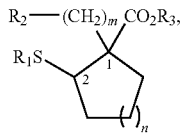

(I)

wherein:

$R_1$ represents a hydrogen atom; a group of formula $COR_4$ wherein $R_4$ represents a linear or branched $C_1$-$C_6$ alkyl group or an aryl group; or a group of formula (A):

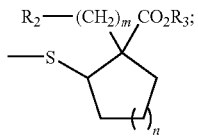

(A)

$R_2$ represents a group of formula $NR_5R_6$ wherein $R_5$ and $R_6$, which may be the same or different, each represent a hydrogen atom or a linear or branched $C_1$-$C_6$ alkyl group, a nitrogen-containing heterocyclic group, an aryl group, or a heteroaryl group;

R3 represents a hydrogen atom or a linear or branched $C_1$-$C_6$ alkyl group;

m represents an integer between 1 and 6 inclusive; and n represents 0, 1, or 2, or an optical isomer thereof, or a pharmaceutically acceptable acid addition salt thereof.

2. The compound of claim 1, wherein $R_1$ represents a hydrogen atom.

3. The compound of claim 1, wherein $R_2$ represents an amino or pyridyl group.

4. The compound of claim 1, wherein $R_3$ represents a hydrogen atom.

5. The compound of formula claim 1, wherein m represents 3.

6. The compound of claim 1, wherein n represents 1.

7. A compound of claim 1 having a structure of formula (Ia):

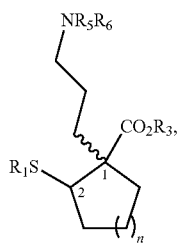

(Ia)

wherein:

$R_1$ represents a hydrogen atom; a group of formula $COR_4$ wherein $R_4$ represents a linear or branched $C_1$-$C_6$ alkyl group or an aryl group; or a group of formula (A):

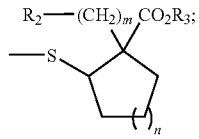

(A)

$R_2$ represents a group of formula $NR_5R_6$ wherein $R_5$ and $R_6$, which may be the same or different, each represent a hydrogen atom or a linear or branched $C_1$-$C_6$ alkyl group, a nitrogen-containing heterocyclic group, an aryl group, or a heteroaryl group;

$R_3$ represents a hydrogen atom or a linear or branched $C_1$-$C_6$ alkyl group;

m represents an integer between 1 and 6 inclusive; and n represents 0, 1, or 2, or an optical isomer thereof, or a pharmaceutically acceptable acid addition salt thereof.

8. The compound of claim 1, which is selected from the group consisting of:

2S)-1-(3-aminopropyl)-2-mercaptocyclopentanecarboxylic acid, (1R,2S)-2-acetylthio-1-(3-aminopropyl)-cyclopentanecarboxylic acid, an optical isomer thereof, and a pharmaceutically acceptable acid addition salt thereof.

9. A pharmaceutical composition comprising a compound of claim 1, in combination with one or more inert, non-toxic, pharmaceutically acceptable excipients or carriers.

10. The pharmaceutical composition of claim 9, further comprising a fibrinolytic, anticoagulant or anti-platelet agent.

11. The pharmaceutical composition of claim 9, wherein the composition is in injectable form and wherein the composition further comprises a fibrinolytic agent selected from recombinant tPA, recombinant uPA and streptokinase.

12. A method for treating a condition selected from the group consisting of myocardial infarction, angina pectoris, arteritis of the lower limbs, venous thromboses, pulmonary embolism, cerebrovascular accidents, vascular complications of diabetes, or aortic aneurysms, the method comprising the step of administering to a patient in need thereof a therapeutically effective amount of a compound of claim 1.

13. The method of claim 12, wherein the compound of claim 1 is administered in combination with a fibrinolytic, anticoagulant or anti-platelet agent.

* * * * *

UNITED STATES PATENT AND TRADEMARK OFFICE
CERTIFICATE OF CORRECTION

PATENT NO.           : 8,309,341 B2                                    Page 1 of 1
APPLICATION NO.      : 12/803405
DATED                : November 13, 2012
INVENTOR(S)          : Philippe Gloanec et al.

It is certified that error appears in the above-identified patent and that said Letters Patent is hereby corrected as shown below:

Column 32, Line 43: "2S)" should be -- (1R, 2S) --

Signed and Sealed this
First Day of January, 2013

David J. Kappos
*Director of the United States Patent and Trademark Office*